United States Patent
Qizilbash

(10) Patent No.: US 11,446,348 B2
(45) Date of Patent: Sep. 20, 2022

(54) VEGETABLE POWDERS, METHODS FOR MANUFACTURING VEGETABLE POWDERS, AND KITS THEREOF

(71) Applicant: Bilal Qizilbash, Flushing, NY (US)

(72) Inventor: Bilal Qizilbash, Flushing, NY (US)

(*) Notice: Subject to any disclaimer, the term of this patent is extended or adjusted under 35 U.S.C. 154(b) by 574 days.

(21) Appl. No.: 16/237,391

(22) Filed: Dec. 31, 2018

(65) Prior Publication Data

US 2019/0201466 A1     Jul. 4, 2019

Related U.S. Application Data

(60) Provisional application No. 62/612,408, filed on Dec. 30, 2017.

(51) Int. Cl.

| | |
|---|---|
| *A61K 36/31* | (2006.01) |
| *A61K 9/48* | (2006.01) |
| *A01N 43/54* | (2006.01) |
| *A01N 37/10* | (2006.01) |
| *A01N 53/00* | (2006.01) |

(52) U.S. Cl.
CPC ............ *A61K 36/31* (2013.01); *A61K 9/4858* (2013.01); *A01N 37/10* (2013.01); *A01N 43/54* (2013.01); *A01N 53/00* (2013.01); *A61K 2236/13* (2013.01); *A61K 2236/15* (2013.01); *A61K 2236/17* (2013.01)

(58) Field of Classification Search
CPC ........ A01N 43/54; A01N 37/10; A01N 53/00; A61K 2236/13; A61K 2236/15; A61K 2236/17; A61K 36/31; A61K 9/4858
See application file for complete search history.

(56) References Cited

U.S. PATENT DOCUMENTS

| | | | | |
|---|---|---|---|---|
| 3,734,751 A | * | 5/1973 | Bengtsson et al. ...... | A23L 19/09 426/271 |
| 3,949,098 A | | 4/1976 | Bangert | |
| 4,220,672 A | * | 9/1980 | Bengtsson ............... | A23L 19/09 426/393 |
| 6,262,284 B1 | | 7/2001 | Khachik | |
| 6,387,434 B1 | * | 5/2002 | Takaoka .................... | A61P 1/00 426/453 |
| 6,416,807 B1 | | 7/2002 | Yamamoto | |
| 6,869,621 B2 | | 3/2005 | Hwang et al. | |
| 6,909,021 B2 | | 6/2005 | Crombie | |
| 8,124,135 B2 | | 2/2012 | Pietrzkowski | |
| 9,919,016 B2 | * | 3/2018 | Qizilbash ............. | A61K 9/0095 |
| 2005/0208138 A1 | | 9/2005 | Yang et al. | |
| 2009/0306219 A1 | | 12/2009 | Presti | |
| 2009/0324705 A1 | | 12/2009 | Vikhrieva | |
| 2014/0271706 A1 | | 9/2014 | Astwood et al. | |
| 2016/0235799 A1 | * | 8/2016 | Qizilbash ............... | A61K 36/31 |

FOREIGN PATENT DOCUMENTS

| | | |
|---|---|---|
| JP | 2004091396 A | 3/2004 |
| JP | 4032072 B1 | 1/2008 |
| WO | 2013062190 A1 | 5/2013 |
| WO | 2014001729 A2 | 1/2014 |
| WO | 2015163442 A1 | 10/2015 |

OTHER PUBLICATIONS

Balance of Nature "Our Process How it's Made" retrieved online Jul. 2021 <URL: balanceofnature.com/our-process?sscid=EAlalQobChMlzor_k5WJ8glVdcqzCh32CATFEAMYAyAAEgKxEPD_BwE&sscid=71k5_scpth>, 4 pages. (Year: 2021).*

By Bak et al., Cooking Process Decreased Nutraceutical Contents and in Vitro Anticancer Effects in Kale Juices, 2007, Cancer Prev Res, vol. 12, pp. 303-309.

Healthjuices, The Benefits of Kale and Kale Juice, Nov. 18, 2013, Healthjuices.net/vegetable-juices/kale/, pp. 1-6. (Year 2013).

Kanengiser, Kale Research Drives Mississippi College Graduate Student, May 9, 2014, University News.

Metz, Timesaver: Freeze Your Smoothies, Aug. 15, 2013, monicametz.com/2013/08/timesaver-freeze-your-smoothies/, pp. 1-3. (Year: 2013).

Olsen et al., Antiproliferative Effects of Fresh and Thermal Processed Green and Red Cultivars of Curly Kale (*Brassica oleracea* L. *convar acephala* var. *sabellica*, Jul. 6, 2012, Journal of Agricultural and Food Chemistry, vol. 60, pp. 7375-7383.

Pavlovic, Elizabeth Brandon, Bilal Qizilbash, Kale Research, Apr. 26, 2014, Real Responsible Eating and Living.

* cited by examiner

*Primary Examiner* — Aaron J Kosar
(74) *Attorney, Agent, or Firm* — Weber Rosselli & Cannon LLP

(57) ABSTRACT

Methods of manufacturing vegetable powders and/or vegetable compositions are described herein.

17 Claims, No Drawings

VEGETABLE POWDERS, METHODS FOR MANUFACTURING VEGETABLE POWDERS, AND KITS THEREOF

CROSS-REFERENCE

The present application claims priority to and the benefit of U.S. Provisional Application Ser. No. 62/612,408 filed on Dec. 30, 2017, the entire contents of which is incorporated herein by reference.

TECHNICAL FIELD

The present disclosure describes vegetable powders and methods for manufacturing vegetable powders. Kits and compositions including the vegetable powders are also described.

BACKGROUND

The war on cancer, which began in 1971, continues with few drugs that selectively kill tumor cells despite the wide array of molecular targets. Tumor cells' astounding adaptability explains much of the poor performance of some of the current therapies. Drugs designed to inactivate certain receptor tyrosine kinases have a brief success that is usually followed by the development of drug resistance. Similarly, drugs designed to induce enough DNA damage to trigger apoptosis are effective until the genes encoding signaling proteins required for cell death become silenced or mutated. Multi-drug resistance can also occur if tumor cells increase their expression of certain ABC transporters in the plasma membrane. Genetically engineered viruses for virotherapy and tumor vaccines designed to enable MHC class I molecules to present tumor antigens to immune cells have shown efficacy in animal studies, yet few such therapies have been tested in humans in large numbers. Drug cocktails are more effective but may worsen side effects and the composition must be adjusted to stay ahead of drug resistance. Adaptation is an emergent property of the cooperation among heterogeneous tumor cells and between tumor cells and stromal cells. The battle raging between clinicians and tumor cells is an arms race with escalating costs and proportionally small decreases in human suffering.

Humans have been gathering and archiving knowledge of medicinal plants for tens of thousands of years. Natural products research provides society with untold numbers of life saving drugs. Several chemotherapies have been developed from plants, e.g. paclitaxel, vincristine, and irinotecan. The treatment of many cellular disorders, for example, tumors, and other hyperproliferative diseases, may involve the systemic use of therapeutic agents. These agents may exert their activity in a variety of ways. In many, if not most instances, the therapeutic agent may not address the abnormal cell specifically, but rather tends to exert its effectiveness systemically across all cells. Systemic administration may therefore expose both abnormal cells and healthy, normal cells to the effects of the therapeutic agent. Although potentially effective therapeutically against the abnormal cells, systemic administration of the therapeutic effect may be detrimental or cause detrimental side effects to the normal healthy cells. This may result in a smaller amount of the intended dosage of the therapeutic agent reaching and addressing the abnormal cells or tumor. In addition, a greater amount of the intended dosage of the therapeutic agent may reach and address the normal healthy cells.

Systemic delivery of therapeutic agents may hinder the dosing parameters from being maximized because of the potentially harmful side effects. In addition, the detrimental effect to the normal healthy cells may weaken and/or cause a decrease in population numbers of the healthy cells thereby decreasing the ability of the healthy cells to fight the proliferation of the abnormal cells.

For example, anti-neoplastic agents may be cytotoxic. The anti-neoplastic agents may exert their cytotoxic activity in a variety of ways, sometimes interfering with a cellular function essential for the replication and/or viability of the cell. Many anti-neoplastic agents may be administered systemically and may not be designed specifically to attack the abnormal cells only, but rather may be designed to exert their effectiveness due to the more rapid proliferation of the abnormal cell, as compared to normal healthy cells. While many organs of the body of a mammalian host regenerate cells rather slowly, there may also be other organs, particularly bone marrow, which involve rapid proliferation of stem cells. Therefore, anti-neoplastic agents may not only affect the slowly regenerating cells detrimentally but may also have a particularly pernicious effect on bone marrow production and the immune system.

Despite the possible disadvantages and side effects of employing the systemic use of therapeutic agents, this method has found extensive application because the agents may have provided some positive results. However, there remains a substantial interest in being able to employ therapeutic agents in a manner which is less systemic, i.e., directed more specifically toward the abnormal cells, while simultaneously protecting sensitive normal cells, in the vicinity of and distant from the site of the abnormal cells. In addition, there remains a need for therapeutic compositions which are directed more specifically toward the abnormal cells while simultaneously promoting proliferation of the normal healthy cells, in the vicinity of and/or distant from the site of abnormal cells.

In addition, there is a general lack of healthy eating amongst the general populations. As evidenced by the increase in cancer-related disease states, as well as the epidemic of obesity, pre-diabetes, diabetes, heart disease, etc., an average person may be more likely to choose an unhealthy food option, which tastes great, over a healthy food option, like vegetables, which may not taste great or have a pleasing texture. Therefore, it would be beneficial to provide a way to infuse the nutrients commonly found in raw vegetables into any food, healthy or unhealthy, in a palatable manner without effecting taste and/or texture of the food.

In addition, the benefits associated with raw vegetables may be further added to non-food items, such as health and beauty aids.

SUMMARY

Vegetable powders and methods of manufacturing such vegetable powders are described herein.

Methods of manufacturing vegetable powder(s) are provided herein and, in some embodiments, include chilling at least one vegetable below ambient room temperature for a period of time to form a chilled vegetable, heating the chilled vegetable to a temperature above ambient room temperature to form at least one dried vegetable, and comminuting the at least one dried vegetable at ambient room temperature to form a vegetable powder.

In some embodiments, the methods of manufacturing vegetable powder(s) further include washing the at least one vegetable prior to chilling, to form at least one washed vegetable.

In some embodiments, the methods of manufacturing vegetable powder(s) further include rinsing the at least one washed vegetable to form at least one rinsed and washed vegetable prior to chilling.

In some embodiments, the methods of manufacturing vegetable powder(s) include freezing at least one vegetable to a temperature below about 0° C. to form a frozen vegetable, heating the at least one frozen vegetable to a temperature above about 30° C. to form at least one dehydrated vegetable, and comminuting the at least one dehydrated vegetable to form a vegetable powder.

In some embodiments, the methods of manufacturing vegetable powder(s) further include washing the at least one vegetable with a detergent in warm water to form at least one washed vegetable, rinsing the washed vegetable in cold water to remove the detergent to form a rinsed vegetable; chilling the washed and rinsed vegetable to a temperature below room temperature to form a chilled vegetable, heating the chilled vegetable to a temperature above room temperature to form a dried vegetable, and comminuting the dried vegetable to form a vegetable powder.

In some embodiments, the methods of manufacturing vegetable powder(s) include washing the at least one whole leaf vegetable with a detergent in warm water to form at least one washed whole leaf vegetable, rinsing the washed whole leaf vegetable in cold water to remove the detergent to form a rinsed whole leaf vegetable, chilling the washed and rinsed whole leaf vegetable to a temperature below room temperature to form a chilled whole leaf vegetable, heating the chilled whole leaf vegetable to a temperature above room temperature to form a dried whole leaf vegetable, and comminuting the dried whole leaf vegetable to form a vegetable powder.

In some embodiments, the methods of manufacturing vegetable powder(s) include washing whole leaf kale with a detergent in warm water to form washed whole leaf kale, rinsing the washed whole leaf kale in cold water to remove the detergent to form a rinsed whole leaf kale; chilling the washed and rinsed whole leaf kale to a temperature below room temperature to form a chilled whole leaf kale, heating the chilled whole leaf kale to a temperature above room temperature to form a dried whole leaf kale, and comminuting the dried whole leaf kale to form a kale powder.

In some embodiments, methods of manufacturing kale powder(s) include freezing whole leaf kale to form frozen whole leaf kale, heating the frozen whole leaf kale to form dehydrated whole leaf kale, and comminuting the dehydrated whole leaf kale to form a kale powder.

In some embodiments, a vegetable powder(s) described herein may include only one type of vegetable, such as only kale. In some embodiments, a vegetable powder(s) described herein may include a combination of vegetables, such as kale and spinach.

In some embodiments, the vegetable powders described herein may include at least 90% of the nutrients of the whole leaf vegetable.

In some embodiments, the vegetable powders described herein may include pesticides in an amount which is less than about 2% of acceptable EPA tolerances, and particularly less than at least 1% of acceptable EPA tolerances.

In some embodiments, the vegetable powders described herein may include at least about 900% of the flavonoids of the whole leaf vegetable.

In some embodiments, a vegetable powder(s) described herein may be combined with at least one additional agent to form a vegetable composition.

In some embodiments, a vegetable composition includes a vegetable powder and at least one of a pharmaceutically acceptable carrier, a therapeutic agent, an optional ingredient, a food-related product, health/beauty aid, and combinations thereof.

In some embodiments, the vegetable powder and/or vegetable composition is placed in a capsule for oral delivery from once to several times per day.

In some embodiments, a vegetable powder and/or vegetable composition may be administered via any appropriate route, including oral, buccal, sublingual, rectal, topical, intranasal, vaginal, parenteral, combinations thereof, and the like.

In some embodiments, a vegetable powder and/or vegetable composition may be used to treat any form of cancer or precancerous lesion including killing cancer cells and/or precancerous cells. In additional embodiments, the vegetable powders and/or vegetable composition may also increase the growth of healthy cells at or near the cancerous or precancerous cells.

In some embodiments, a vegetable powder and/or vegetable composition is added to a liquid and frozen to provide vegetable powder and/or vegetable composition ice cubes. In some embodiments, the liquid is water.

Kits including a vegetable powder and/or vegetable composition and a container are also described. In some embodiments, the container is a shaker. In some embodiments, the container is a sealable plastic bag.

DETAILED DESCRIPTION

The methods described herein produce a vegetable powder suitable for animal, and particularly human, consumption. The vegetables powders configured to maintain a predominant amount of the nutrients of the natural raw whole leaf version of the vegetable thereby offering the consumer of the vegetable powder the nutritious benefits of the natural raw whole leaf vegetable without the less pleasing taste and/or texture of the natural raw whole leaf version of the vegetable. Any vegetable(s) may be used in such methods to produce a suitable vegetable powder. Some non-limiting examples of suitable vegetables include leafy vegetables, flower bud vegetables, bulb (and/or stem) vegetables, root vegetables, and combinations thereof.

The vegetables may be grown organically or inorganically, i.e., not grown organically. In some embodiments, the vegetables may be grown with the use of pesticides, herbicides, and/or insecticides. Some non-limiting examples of pesticides used to grow the vegetables described herein includes azoxystrobin, bifethrin, dacthal, boscalid, DEET, and the like.

In some embodiments, the vegetable powder includes at least one leafy vegetable. Some non-limiting examples of suitable leafy vegetables include arugula, bok choy, cabbage, lettuce, radicchio, spinach, kale, and combinations thereof. In some embodiments, the leafy vegetable is a green leafy vegetable.

In some embodiments, the leafy vegetable is arugula. In some embodiments, the leafy vegetable is bok choy. In some embodiments, the leafy vegetable is cabbage. In some embodiments, the leafy vegetable is lettuce. In some embodiments, the leafy vegetable is radicchio. In some embodiments, the leafy vegetable is spinach.

In some embodiments, the leafy vegetable is kale. Kale is a vegetable within the plant species *Brassica oleracea*. Some non-limiting examples of kale include curly-leaf kale, plain-leaf kale, rape leaf kale, leaf and spear kale, bumpy-leaf kale, baby kale, and ornamental kale. In some embodiments, the powders described herein include kale derived from curly-leaf kale and/or baby kale.

In some embodiments, the kale may be grown organically. In some embodiments, the kale may be grown without the use of pesticides, herbicides, and/or insecticides.

In some embodiments, the kale may be grown inorganically, i.e., not grown organically. In some embodiments, the kale may be grown with the use of pesticides, herbicides, and/or insecticides. Some non-limiting examples of pesticides, herbicides, and/or insecticides used to grow kale include azoxystrobin, bifethrin, dacthal, boscalid, DEET, and the like.

The vegetable powders described herein may be made from vegetables grown inorganically, wherein the powders include a reduced amount of pesticides, herbicides, and/or insecticides as compared to known EPA tolerances, as well as compared to other known vegetable powders made from inorganically grown vegetables.

In some embodiments, the vegetable(s) used in the processes described herein may be processed in a natural and/or raw whole leaf format. The phrase raw whole leaf format is intended to include a natural version of the vegetable as a whole and is intended to encompass not only the leaf, for leafy vegetables, but also the flower, bud, stem, bulb, or root of the certain vegetable to be processed. For example, the powders described herein may be derived from a raw whole leaf of the selected leafy vegetable, i.e., kale, that is processed as described herein. In another example, the powders described herein may be derived from a raw whole leaf of a flower vegetable, i.e., artichoke, that is processed as described herein. In some embodiments, a raw whole leaf of the selected vegetable(s) is processed, i.e., washed, rinsed, chilled, dried, and/or comminuted, to produce the powders described herein.

In some embodiments, at least one whole leaf of kale is processed, i.e., washed, chilled, dehydrated, and/or comminuted, to produce a kale powder. In some embodiments, the whole leaf kale may be combined with other vegetables to produce a vegetable powder including a combination of vegetables.

In some embodiments, the vegetable powder includes at least one flower vegetable. Some non-limiting examples of suitable flower vegetables include artichoke, capers, cauliflower, broccoli, broccolini, and combinations thereof. In some embodiments, the at least one flower vegetable is a green flower vegetable.

In some embodiments, the flower vegetable is artichoke. In some embodiments, the flower vegetable is caper. In some embodiments, the flower vegetable is cauliflower. In some embodiments, the flower vegetable is broccoli. In some embodiments, the flower vegetable is broccolini.

In some embodiments, the flower vegetable(s) used in the processes described herein may be processed in a natural and/or whole format. For example, the powders described herein may be derived from a whole of the selected flower vegetable that is processed as described herein. In some embodiments, a whole flower of the selected flower vegetable(s) is processed, i.e., washed, rinsed, chilled, dried, and/or comminuted, to produce the powders described herein. For example, in some embodiments and without limitation, a whole natural artichoke and/or natural cauliflower is processed to form a vegetable powder.

In some embodiments, the vegetable powder includes at least one bulb vegetable. Some non-limiting examples of suitable bulb vegetables include asparagus, celery, chives, garlic, fennel, kohlrabi, onions, lotus root, leek, celeriac, and combinations thereof. In some embodiments, the at least one bulb vegetable is a green bulb vegetable.

In some embodiments, the bulb vegetable is asparagus. In some embodiments, the bulb vegetable is celery. In some embodiments, the bulb vegetable is chive. In some embodiments, the bulb vegetable is garlic. In some embodiments, the bulb vegetable is fennel. In some embodiments, the bulb vegetable is kohlrabi. In some embodiments, the bulb vegetable is onion.

In some embodiments, the bulb vegetable is lotus root. In some embodiments, the bulb vegetable is leek. In some embodiments, the bulb vegetable is celeriac.

In some embodiments, the bulb vegetable(s) used in the processes described herein may be processed in a natural and/or whole format. For example, the powders described herein may be derived from a whole of the selected bulb vegetable that is processed as described herein. In some embodiments, a whole bulb of the selected bulb vegetable(s) is processed, i.e., washed, rinsed, chilled, heated, and/or comminuted, to produce the powders described herein. For example, in some embodiments and without limitation, a whole natural fennel and/or natural celery is processed to form a vegetable powder.

In some embodiments, the vegetable powder includes at least one root vegetable. Some non-limiting examples of suitable root vegetables include carrots, bamboo shoot, potato, radish, sweet potato, yam, water chestnut, and combinations thereof. In some embodiments, the at least one root vegetable is an orange root vegetable. In some embodiments, the root vegetable is carrot. In some embodiments, the root vegetable is bamboo shoot. In some embodiments, the root vegetable is radish. In some embodiments, the root vegetable is sweet potato. In some embodiments, the root vegetable is yam.

In some embodiments, the root vegetable(s) used in the processes described herein may be processed in a natural and/or whole format. For example, the powders described herein may be derived from a whole of the selected root vegetable that is processed as described herein. In some embodiments, a whole of the selected root vegetable(s) is processed, i.e., washed, chilled, dehydrated, and/or comminuted, to produce the powders described herein. For example, in some embodiments and without limitation, a whole natural carrot and/or natural sweet potato is processed including any outer skin, if applicable. In some embodiments, the vegetables described herein may also be peeled to remove an outer skin, if applicable and processed in whole without an outer skin, such as may be the case with a sweet potato or yam.

As noted throughout the present disclosure, the methods described herein produce a vegetable powder. By powder, the vegetable(s) processed are reduced to an average particle size of less than 1 mm. For example, in some embodiments, the vegetables are comminuted to form powders having an average particle size having a mean diameter ranging from about 0.1 microns to about 500 microns. In some embodiments, the powders may include an average particle size having a mean diameter ranging from about 1 micron to about 300 microns. In still other embodiments, the powders may include an average particle size having a mean diameter ranging from about 5 microns to about 250 microns. In still other embodiments, the powders may include an average particle size having a mean diameter ranging from about 10 microns to about 150 microns. In still other embodiments, the powders may include an average particle size having a mean diameter ranging from about 15 microns to about 100 microns. In still other embodiments, the powders may include an average particle size having a mean diameter ranging from about 20 microns to about 75 microns.

In addition, the vegetable powders are powders having a moisture content less than about 10% by weight. In some embodiments, the vegetable powders are powders having a moisture content less than about 7.5% by weight. In some embodiments, the vegetable powders are powders having a moisture content less than about 5% by weight. In some embodiments, the powders may include a moisture content less than about 2.5% by weight. In still other embodiments, the powders may include a moisture content less than about 1% by weight. In still other embodiments, the powders may include a moisture content less than about 0.75% by weight. In still other embodiments, the powders may include a moisture content less than about 0.5% by weight. In still other embodiments, the powders may include a moisture content less than about 0.25% by weight. In still other embodiments, the powders may include a moisture content less than about 0.1% by weight. In still other embodiments, the powders are dry powders free of any moisture and/or having a moisture content of 0%.

In some embodiments, the vegetable powders described herein include an average particle size having a mean diameter ranging from about 0.1 microns to about 500 microns and a moisture content of less than about 10% by weight.

In some embodiments, the vegetable powders described herein include an average particle size having a mean diameter ranging from about 0.1 microns to about 500 microns and a moisture content of less than about 7.5% by weight.

In some embodiments, the vegetable powders described herein include an average particle size having a mean diameter ranging from about 0.1 microns to about 500 microns and a moisture content of less than about 5% by weight.

In some embodiments, the vegetable powders described herein include an average particle size having a mean diameter ranging from about 0.1 microns to about 500 microns and a moisture content of less than about 2.5% by weight.

In some embodiments, the vegetable powders described herein include an average particle size having a mean diameter ranging from about 0.1 microns to about 500 microns and a moisture content of less than about 1% by weight.

In some embodiments, the vegetable powders described herein include an average particle size having a mean diameter ranging from about 0.1 microns to about 500 microns and a moisture content of less than about 0.75% by weight.

In some embodiments, the vegetable powders described herein include an average particle size having a mean diameter ranging from about 0.1 microns to about 500 microns and a moisture content of less than about 0.5% by weight.

In some embodiments, the vegetable powders described herein include an average particle size having a mean diameter ranging from about 0.1 microns to about 500 microns and a moisture content of less than about 0.25% by weight.

In some embodiments, the vegetable powders described herein include an average particle size having a mean diameter ranging from about 0.1 microns to about 500 microns and a moisture content of less than about 0.1% by weight.

In some embodiments, the vegetable powders described herein include an average particle size having a mean diameter ranging from about 0.1 microns to about 500 microns and are a dry powder having a moisture content of 0% by weight.

In some embodiments, the vegetable powders described herein include an average particle size having a mean diameter ranging from about 1 microns to about 300 microns and a moisture content of less than about 10% by weight.

In some embodiments, the vegetable powders described herein include an average particle size having a mean diameter ranging from about 1 microns to about 300 microns and a moisture content of less than about 7.5% by weight.

In some embodiments, the vegetable powders described herein include an average particle size having a mean diameter ranging from about 1 microns to about 300 microns and a moisture content of less than about 5% by weight.

In some embodiments, the vegetable powders described herein include an average particle size having a mean diameter ranging from about 1 microns to about 300 microns and a moisture content of less than about 2.5% by weight.

In some embodiments, the vegetable powders described herein include an average particle size having a mean diameter ranging from about 1 microns to about 300 microns and a moisture content of less than about 1% by weight.

In some embodiments, the vegetable powders described herein include an average particle size having a mean diameter ranging from about 1 microns to about 300 microns and a moisture content of less than about 0.75% by weight.

In some embodiments, the vegetable powders described herein include an average particle size having a mean diameter ranging from about 1 microns to about 300 microns and a moisture content of less than about 0.5% by weight.

In some embodiments, the vegetable powders described herein include an average particle size having a mean diameter ranging from about 1 microns to about 300 microns and a moisture content of less than about 0.25% by weight.

In some embodiments, the vegetable powders described herein include an average particle size having a mean diameter ranging from about 1 microns to about 300 microns and a moisture content of less than about 0.1% by weight.

In some embodiments, the vegetable powders described herein include an average particle size having a mean diameter ranging from about 1 microns to about 300 microns and are a dry powder having a moisture content of 0% by weight.

In some embodiments, the vegetable powders described herein include an average particle size having a mean diameter ranging from about 5 microns to about 250 microns and a moisture content of less than about 10% by weight.

In some embodiments, the vegetable powders described herein include an average particle size having a mean diameter ranging from about 5 microns to about 250 microns and a moisture content of less than about 7.5% by weight.

In some embodiments, the vegetable powders described herein include an average particle size having a mean diameter ranging from about 5 microns to about 250 microns and a moisture content of less than about 5% by weight.

In some embodiments, the vegetable powders described herein include an average particle size having a mean diameter ranging from about 5 microns to about 250 microns and a moisture content of less than about 2.5% by weight.

In some embodiments, the vegetable powders described herein include an average particle size having a mean diameter ranging from about 5 microns to about 250 microns and a moisture content of less than about 1% by weight.

In some embodiments, the vegetable powders described herein include an average particle size having a mean diameter ranging from about 5 microns to about 250 microns and a moisture content of less than about 0.75% by weight.

In some embodiments, the vegetable powders described herein include an average particle size having a mean diameter ranging from about 5 microns to about 250 microns and a moisture content of less than about 0.5% by weight.

In some embodiments, the vegetable powders described herein include an average particle size having a mean diameter ranging from about 5 microns to about 250 microns and a moisture content of less than about 0.25% by weight.

In some embodiments, the vegetable powders described herein include an average particle size having a mean diameter ranging from about 5 microns to about 250 microns and a moisture content of less than about 0.1% by weight.

In some embodiments, the vegetable powders described herein include an average particle size having a mean diameter ranging from about 5 microns to about 250 microns and are a dry powder having a moisture content of 0% by weight.

In some embodiments, the vegetable powders described herein include an average particle size having a mean diameter ranging from about 10 microns to about 150 microns and a moisture content of less than about 10% by weight.

In some embodiments, the vegetable powders described herein include an average particle size having a mean diameter ranging from about 10 microns to about 150 microns and a moisture content of less than about 7.5% by weight.

In some embodiments, the vegetable powders described herein include an average particle size having a mean diameter ranging from about 10 microns to about 150 microns and a moisture content of less than about 5% by weight.

In some embodiments, the vegetable powders described herein include an average particle size having a mean diameter ranging from about 10 microns to about 150 microns and a moisture content of less than about 2.5% by weight.

In some embodiments, the vegetable powders described herein include an average particle size having a mean diameter ranging from about 10 microns to about 150 microns and a moisture content of less than about 1% by weight.

In some embodiments, the vegetable powders described herein include an average particle size having a mean diameter ranging from about 10 microns to about 150 microns and a moisture content of less than about 0.75% by weight.

In some embodiments, the vegetable powders described herein include an average particle size having a mean diameter ranging from about 10 microns to about 150 microns and a moisture content of less than about 0.5% by weight.

In some embodiments, the vegetable powders described herein include an average particle size having a mean diameter ranging from about 10 microns to about 150 microns and a moisture content of less than about 0.25% by weight.

In some embodiments, the vegetable powders described herein include an average particle size having a mean diameter ranging from about 10 microns to about 150 microns and a moisture content of less than about 0.1% by weight.

In some embodiments, the vegetable powders described herein include an average particle size having a mean diameter ranging from about 10 microns to about 150 microns and are a dry powder having a moisture content of 0% by weight.

In some embodiments, the vegetable powders described herein include an average particle size having a mean diameter ranging from about 15 microns to about 100 microns and a moisture content of less than about 10% by weight.

In some embodiments, the vegetable powders described herein include an average particle size having a mean diameter ranging from about 15 microns to about 100 microns and a moisture content of less than about 7.5% by weight.

In some embodiments, the vegetable powders described herein include an average particle size having a mean diameter ranging from about 15 microns to about 100 microns and a moisture content of less than about 5% by weight.

In some embodiments, the vegetable powders described herein include an average particle size having a mean diameter ranging from about 15 microns to about 100 microns and a moisture content of less than about 2.5% by weight.

In some embodiments, the vegetable powders described herein include an average particle size having a mean diameter ranging from about 15 microns to about 100 microns and a moisture content of less than about 1% by weight.

In some embodiments, the vegetable powders described herein include an average particle size having a mean diameter ranging from about 15 microns to about 100 microns and a moisture content of less than about 0.75% by weight.

In some embodiments, the vegetable powders described herein include an average particle size having a mean diameter ranging from about 15 microns to about 100 microns and a moisture content of less than about 0.5% by weight.

In some embodiments, the vegetable powders described herein include an average particle size having a mean diameter ranging from about 15 microns to about 100 microns and a moisture content of less than about 0.25% by weight.

In some embodiments, the vegetable powders described herein include an average particle size having a mean diameter ranging from about 15 microns to about 100 microns and a moisture content of less than about 0.1% by weight.

In some embodiments, the vegetable powders described herein include an average particle size having a mean diameter ranging from about 15 microns to about 100 microns and are a dry powder having a moisture content of 0% by weight.

In some embodiments, the vegetable powders described herein include an average particle size having a mean diameter ranging from about 20 microns to about 75 microns and a moisture content of less than about 10% by weight.

In some embodiments, the vegetable powders described herein include an average particle size having a mean diameter ranging from about 20 microns to about 75 microns and a moisture content of less than about 7.5% by weight.

In some embodiments, the vegetable powders described herein include an average particle size having a mean diameter ranging from about 20 microns to about 75 microns and a moisture content of less than about 5% by weight.

In some embodiments, the vegetable powders described herein include an average particle size having a mean diameter ranging from about 20 microns to about 75 microns and a moisture content of less than about 2.5% by weight.

In some embodiments, the vegetable powders described herein include an average particle size having a mean diameter ranging from about 20 microns to about 75 microns and a moisture content of less than about 1% by weight.

In some embodiments, the vegetable powders described herein include an average particle size having a mean diameter ranging from about 20 microns to about 75 microns and a moisture content of less than about 0.75% by weight.

In some embodiments, the vegetable powders described herein include an average particle size having a mean diameter ranging from about 20 microns to about 75 microns and a moisture content of less than about 0.5% by weight.

In some embodiments, the vegetable powders described herein include an average particle size having a mean diameter ranging from about 20 microns to about 75 microns and a moisture content of less than about 0.25% by weight.

In some embodiments, the vegetable powders described herein include an average particle size having a mean diameter ranging from about 20 microns to about 75 microns and a moisture content of less than about 0.1% by weight.

In some embodiments, the vegetable powders described herein include an average particle size having a mean diameter ranging from about 20 microns to about 75 microns and are a dry powder having a moisture content of 0% by weight.

Methods of producing and/or manufacturing a vegetable powder are described herein. The methods include at least the steps of: chilling at least one vegetable to form at least one chilled vegetable; heating the at least one chilled vegetable to form at least one dried vegetable; and comminuting the at least one dried vegetable to form a powder. In some embodiments, the methods further include the step of washing the at least one vegetable with a soap and/or surfactant to form at least one washed vegetable, prior to the step of chilling. In some embodiments, the methods further include the step of rinsing the at least one washed vegetable, after the step of washing to form at least one rinsed vegetable, and prior to the step of chilling.

The step of chilling the at least one vegetable includes exposing the vegetable(s) to a temperature below ambient and/or room temperature, i.e., less than about 15° C. In some embodiments, the vegetable(s) may be chilled by exposure to a temperature below about 10° C. In some embodiments, the vegetable(s) may be chilled by exposure to a temperature below about 5° C. In some embodiments, the vegetable(s) may be chilled or frozen by exposure to a temperature below about 0° C. In some embodiments, the vegetable(s) may be chilled or frozen by exposure to a temperature below about −5° C. In some embodiments, the vegetable(s) may be chilled or frozen by exposure to a temperature below about −10° C. In some embodiments, the vegetable(s) may be chilled or frozen by exposure to a temperature below about −15° C. In some embodiments, the vegetable(s) may be chilled or frozen by exposure to a temperature below about −20° C. In some embodiments, the vegetable(s) may be chilled or frozen by exposure to a temperature below about −100° C.

In still other embodiments, the vegetable(s) may be chilled or frozen by exposure to a temperature ranging from about −250° C. to about 10° C. In still other embodiments, the vegetable(s) may be chilled by exposure to a temperature ranging from about −100° C. to about 5° C. In still other embodiments, the vegetable(s) may be chilled by exposure to a temperature ranging from about −50° C. to about 0° C. In still other embodiments, the vegetable(s) may be chilled by exposure to a temperature ranging from about −35° C. to about −5° C. In still other embodiments, the vegetable(s) may be chilled by exposure to a temperature ranging from about −20° C. to about −10° C. In still other embodiments, the vegetable(s) may be chilled by exposure to a temperature ranging from about −200° C. to about −100° C.

In some embodiments, the step of chilling may include exposing the at least one vegetable to a temperature below the vegetable's freezing point thereby forming at least one frozen vegetable. Since the freezing point for each vegetable will vary, in some embodiments, some methods include the step of chilling and/or freezing at least one vegetable. By freezing, the vegetable(s) are exposed to temperatures at or below their respective freezing temperature points for sufficient amount of time for the vegetable to become frozen. Some non-limiting examples include flash freezing and/or mechanical freezing. Mechanical freezing utilizes refrigerants and pressure to mechanically lower temperatures. Some examples of mechanical freezers include chest freezers, drawer freezers, upright freezers, portable freezers, air blast freezers, box freezers, fluidized bed freezers, immersion freezers, contact belt freezers, and impingement freezers. Cryogenic freezers may be used in flash freezing.

By chilling and/or freezing at least one vegetable, the at least one vegetable may be exposed to a decrease in temperature for any amount of time suitable for maintaining the edibility of the vegetable(s) and prior to further processing, such as heating or powdering. For example, the vegetable(s) may be chilled: in some embodiments, for up to six months; in some embodiments, for up to 3 months; in some embodiments, for up to 1 month; in some embodiments, for up to 3 weeks; in some embodiments, for up to 2 weeks; in some embodiments, for up to 1 week; in some embodiments, for up to 5 days; in some embodiments, for up to 3 days; in some embodiments, for up to 24 hours; in some embodiments, for up to 12 hours; in some embodiments, for up to 6 hours; in some embodiments, for up to 1 hour; in some embodiments, for up to 30 minutes; in some embodiments, for up to 15 minutes; in some embodiments, for up to 5 minutes.

The manners in which the vegetable(s) are chilled may be selected from the use of ice, dry ice, ice baths, refrigeration, air conditioning, and/or freezers. In some embodiments, the vegetable(s) is frozen using any suitable method including, but not limited to, flash freezing, cryogenic freezing, slow freezing, blast freezing, and airblast freezers.

Once the whole leaf vegetable is chilled and/or frozen, the methods for manufacturing the vegetable powders described herein include the step of heating the at least one chilled (and/or frozen) whole leaf vegetable by exposing the chilled vegetable(s) to a temperature above ambient and/or room temperature, i.e., greater than about 85° Fahrenheit (F) to dry the chilled vegetable(s). In some embodiments, the chilled vegetable(s) may be heated to a temperature above about 90° F. In some embodiments, the chilled vegetable(s) may be heated to a temperature above about 95° F. In some embodiments, the chilled vegetable(s) may be heated to a temperature above about 100° F. In some embodiments, the chilled vegetable(s) may be heated to a temperature above about 105° F. In some embodiments, the chilled vegetable(s) may be heated to a temperature above about 110° F. In some embodiments, the chilled vegetable(s) may be heated to a temperature above about 115° F. In some embodiments, the chilled vegetable(s) may be heated to a temperature above about 120° F. In some embodiments, the chilled vegetable(s) may be heated to a temperature above about 125° F. In some embodiments, the chilled vegetable(s) may be heated to a temperature above about 130° F. In some embodiments, the chilled vegetable(s) may be heated to a temperature above about 135° F. In some embodiments, the vegetable(s) may be heated to a temperature above about 140° F. In some embodiments, the chilled vegetable(s) may be heated to a temperature above about 145° F. In some embodiments, the chilled vegetable(s) may be heated to a temperature above about 150° F. In some embodiments, the chilled vegetable(s) may be heated to a temperature above about 155° F. In some embodiments, the chilled vegetable(s) may be heated to a temperature above about 160° F.

In still other embodiments, the chilled whole leaf vegetable(s) may be heated to a temperature ranging from about 85° F. to about 160° F. In still other embodiments, the chilled vegetable(s) may be heated to a temperature ranging from about 90° F. to about 150° F. In still other embodiments, the chilled vegetable(s) may be heated to a temperature ranging from about 95° F. to about 140° F. In still other embodiments, the chilled vegetable(s) may be heated to a temperature ranging from about 100° F. to about 120° F. In still other embodiments, the chilled vegetable(s) may be heated to a temperature ranging from about 90° F. to about 115° F. In still other embodiments, the chilled vegetable(s) may be heated to a temperature ranging from about 95° F. to about 110° F. In yet other embodiments, the chilled vegetable(s) may be heated to a temperature ranging from about 96° F. to about 106° F. The whole leaf vegetables described herein are never blanched or steamed or exposed to high temperatures exceeding about 160° C.

By the step(s) of heating described herein, the at least one chilled vegetable may be exposed to an increase in temperature to dry and/or dehydrate the at least one vegetable for any amount of time suitable for maintaining the edibility of the vegetable(s) and/or without cooking the at least one chilled vegetable. By cooking, the vegetable(s) may be exposed to temperatures high enough to break down the nutritional benefits, i.e., vitamins, minerals, antioxidants, fiber, proteins, flavonoids, and the like, found in naturally raw vegetable(s). In some embodiments, exposing the whole leaf vegetable to the temperature below about 150° F. may assist with preventing the loss of nutritional value of a given vegetable. In some embodiments, exposing the whole leaf vegetable to the temperature below about 125° F. may assist with preventing the loss of nutritional value of a given vegetable. In some embodiments, exposing whole leaf kale to the temperature below about 115° F. may assist with preventing the loss of nutritional value of a given vegetable. Thus, avoiding the use of higher temperatures to dry the vegetable(s) allows the dried and/or dehydrated vegetable(s) to maintain a maximum amount of the nutritional benefits of the naturally raw hydrated (non-dried and/or non-dehydrated) vegetable(s).

The length of time required for heating, drying and/or dehydrating the chilled vegetable(s) can depend upon the amount of water and/or moisture content found in the chilled and/or frozen vegetable(s) and/or the temperature at which the vegetable(s) are dried. In some embodiments, the larger the amount of water and/or moisture content in the chilled vegetable(s), the larger the amount of time needed to dry and/or dehydrate the vegetable(s). In some embodiments, the lower the temperature at which the vegetable(s) are dried, the larger the amount of time needed to dry and/or dehydrate the vegetable(s). For example, the vegetable(s) may be heated: in some embodiments, for up to six months; in some embodiments, for up to 3 months; in some embodiments, for up to 1 month; in some embodiments, for up to 3 weeks; in some embodiments, for up to 2 weeks; in some embodiments, for up to 1 week; in some embodiments, for up to 5 days; in some embodiments, for up to 3 days; in some embodiments, for up to 24 hours; in some embodiments, for up to 12 hours; in some embodiments, for up to 6 hours; in some embodiments, for up to 1 hour; in some embodiments, for up to 30 minutes; in some embodiments, for up to 15 minutes; in some embodiments, for up to 5 minutes.

The manners in which the vegetable(s) are heated may be selected from the use of ovens, kilns, fire, heaters, boilers, dehydrators, and the like. In some embodiments, the chilled vegetable(s) are heated using a linear or vertical dehydrator. It is envisioned that the need to maintain a controlled temperature for a predetermined amount of time prevents and/or decreases the possibility of the chilled vegetable(s) of being destroyed by cooking and/or thermal breakdown due to exposure to high temperatures.

In some embodiments, the chilled vegetable(s) may be heated to a temperature ranging from about 85° F. to about 120° F. for up to 72 hours.

In some embodiments, the chilled vegetable(s) may be heated to a temperature ranging from about 85° F. to about 120° F. for up to 48 hours.

In some embodiments, the chilled vegetable(s) may be heated to a temperature ranging from about 85° F. to about 120° F. for up to 24 hours.

In some embodiments, the chilled vegetable(s) may be heated to a temperature ranging from about 85° F. to about 120° F. for up to 18 hours.

In some embodiments, the chilled vegetable(s) may be heated to a temperature ranging from about 85° F. to about 120° F. for up to 12 hours.

In some embodiments, the chilled vegetable(s) may be heated to a temperature ranging from about 85° F. to about 120° F. for up to 8 hours.

In some embodiments, the chilled vegetable(s) may be heated to a temperature ranging from about 85° F. to about 120° F. for up to 6 hours.

In some embodiments, the chilled vegetable(s) may be heated to a temperature ranging from about 85° F. to about 120° F. for up to 4 hours.

In some embodiments, the chilled vegetable(s) may be heated to a temperature ranging from about 85° F. to about 120° F. for up to 2 hours.

In some embodiments, the chilled vegetable(s) may be heated to a temperature ranging from about 85° F. to about 120° F. for up to 1 hour.

In some embodiments, the chilled vegetable(s) may be heated to a temperature ranging from about 85° F. to about 120° F. for up to 30 minutes.

In some embodiments, the chilled vegetable(s) may be heated to a temperature ranging from about 85° F. to about 120° F. from 2 to 12 hours.

In some embodiments, the chilled vegetable(s) may be heated to a temperature ranging from about 85° F. to about 120° F. from 3 to 6 hours.

In some embodiments, the chilled vegetable(s) may be heated to a temperature ranging from about 90° F. to about 115° F. for up to 72 hours.

In some embodiments, the chilled vegetable(s) may be heated to a temperature ranging from about 90° F. to about 115° F. for up to 48 hours.

In some embodiments, the chilled vegetable(s) may be heated to a temperature ranging from about 90° F. to about 115° F. for up to 24 hours.

In some embodiments, the chilled vegetable(s) may be heated to a temperature ranging from about 90° F. to about 115° F. for up to 18 hours.

In some embodiments, the chilled vegetable(s) may be heated to a temperature ranging from about 90° F. to about 115° F. for up to 12 hours.

In some embodiments, the chilled vegetable(s) may be heated to a temperature ranging from about 90° F. to about 115° F. for up to 8 hours.

In some embodiments, the chilled vegetable(s) may be heated to a temperature ranging from about 90° F. to about 115° F. for up to 6 hours.

In some embodiments, the chilled vegetable(s) may be heated to a temperature ranging from about 90° F. to about 115° F. for up to 4 hours.

In some embodiments, the chilled vegetable(s) may be heated to a temperature ranging from about 90° F. to about 115° F. for up to 2 hours.

In some embodiments, the chilled vegetable(s) may be heated to a temperature ranging from about 90° F. to about 115° F. for up to 1 hour.

In some embodiments, the chilled vegetable(s) may be heated to a temperature ranging from about 90° F. to about 115° F. for up to 30 minutes.

In some embodiments, the chilled vegetable(s) may be heated to a temperature ranging from about 90° F. to about 115° F. from 2 to 12 hours.

In some embodiments, the chilled vegetable(s) may be heated to a temperature ranging from about 90° F. to about 115° F. from 3 to 6 hours.

In some embodiments, the chilled vegetable(s) may be heated to a temperature ranging from about 95° F. to about 110° F. for up to 72 hours.

In some embodiments, the chilled vegetable(s) may be heated to a temperature ranging from about 95° F. to about 110° F. for up to 48 hours.

In some embodiments, the chilled vegetable(s) may be heated to a temperature ranging from about 95° F. to about 110° F. for up to 24 hours.

In some embodiments, the chilled vegetable(s) may be heated to a temperature ranging from about 95° F. to about 110° F. for up to 18 hours.

In some embodiments, the chilled vegetable(s) may be heated to a temperature ranging from about 95° F. to about 110° F. for up to 12 hours.

In some embodiments, the chilled vegetable(s) may be heated to a temperature ranging from about 95° F. to about 110° F. for up to 8 hours.

In some embodiments, the chilled vegetable(s) may be heated to a temperature ranging from about 95° F. to about 110° F. for up to 6 hours.

In some embodiments, the chilled vegetable(s) may be heated to a temperature ranging from about 95° F. to about 110° F. for up to 4 hours.

In some embodiments, the chilled vegetable(s) may be heated to a temperature ranging from about 95° F. to about 110° F. for up to 2 hours.

In some embodiments, the chilled vegetable(s) may be heated to a temperature ranging from about 95° F. to about 110° F. for up to 1 hour.

In some embodiments, the chilled vegetable(s) may be heated to a temperature ranging from about 95° F. to about 110° F. for up to 30 minutes.

In some embodiments, the chilled vegetable(s) may be heated to a temperature ranging from about 95° F. to about 110° F. from 2 to 12 hours.

In some embodiments, the chilled vegetable(s) may be heated to a temperature ranging from about 95° F. to about 110° F. from 3 to 6 hours.

In some embodiments, the chilled vegetable(s) may be heated to a temperature ranging from about 100° F. to about 106° F. for up to 72 hours.

In some embodiments, the chilled vegetable(s) may be heated to a temperature ranging from about 100° F. to about 106° F. for up to 48 hours.

In some embodiments, the chilled vegetable(s) may be heated to a temperature ranging from about 100° F. to about 106° F. for up to 24 hours.

In some embodiments, the chilled vegetable(s) may be heated to a temperature ranging from about 100° F. to about 106° F. for up to 18 hours.

In some embodiments, the chilled vegetable(s) may be heated to a temperature ranging from about 100° F. to about 106° F. for up to 12 hours.

In some embodiments, the chilled vegetable(s) may be heated to a temperature ranging from about 100° F. to about 106° F. for up to 8 hours.

In some embodiments, the chilled vegetable(s) may be heated to a temperature ranging from about 100° F. to about 106° F. for up to 6 hours.

In some embodiments, the chilled vegetable(s) may be heated to a temperature ranging from about 100° F. to about 106° F. for up to 4 hours.

In some embodiments, the chilled vegetable(s) may be heated to a temperature ranging from about 100° F. to about 106° F. for up to 2 hours.

In some embodiments, the chilled vegetable(s) may be heated to a temperature ranging from about 100° F. to about 106° F. for up to 1 hour.

In some embodiments, the chilled vegetable(s) may be heated to a temperature ranging from about 100° F. to about 106° F. for up to 30 minutes.

In some embodiments, the chilled vegetable(s) may be heated to a temperature ranging from about 100° F. to about 106° F. from 2 to 12 hours.

In some embodiments, the chilled vegetable(s) may be heated to a temperature ranging from about 100° F. to about 106° F. from 3 to 6 hours.

As noted hereinabove, the vegetable(s) may be chilled and/or dried in the vegetable's natural raw and/or whole form, i.e., as a bulb, as a leaf, as a stem, as a root, of the specific vegetable(s). For example, in some embodiments, the at least one vegetable is kale (a leafy vegetable naturally made of leaves) and the kale leaves are chilled and/or dried as whole leaves.

Obviously, leaves can be damaged during harvesting and processing, so the present use of the word "whole" is not intended to require only completely full leaves (bulbs, flowers, roots, buds, etc.), but rather intended to indicate that the leaves are processed as the leaves naturally exist and/or are naturally found. In other words, the whole leaves are not comminuted and/or broken down into smaller chunks and/or pieces prior to washing, rinsing, chilling and/or heating of the vegetable.

In some embodiments, the only time the vegetable(s) are broken down into smaller pieces is after the vegetable(s) has been washed, rinsed, chilled, and/or dried.

In some embodiments, the dried vegetable(s) are broken down into a smaller particulate, i.e., powder, via the step of comminuting.

In some embodiments, the step of comminuting the dried vegetable(s) includes the reduction of the solid material of the vegetable(s) from a larger more natural size to a smaller free-flowing powder size. The step of comminuting of the vegetable(s) can be performed by cutting, grinding, milling, grating, lasering, vibrating, centrifugation, and/or crushing of the vegetable(s). In some embodiments, the dried vegetable(s) may be ground into smaller pieces using a commercial grinder. In some embodiments, the dried vegetable(s) may be ground into smaller pieces using a mortar and pestle. In some embodiments, the dried vegetable(s) may be crushed into smaller pieces using a crusher. In some embodiments, the dried vegetables may be dry blended into smaller pieces using a blender or juicer. In some embodiments, the dried vegetable may be cryogenically milled into smaller pieces.

In some embodiments, the at least one whole leaf vegetable may be initially washed with a soap, detergent, and/or surfactant. By washing the at least one vegetable, it is envisioned that the outer surface of the at least one vegetable is removed of dirt and residues. In addition, the outer surface of the least one vegetable may have an outer coating on the vegetable removed. For example, kale includes an outer coating that is removed when washed to produce a shinier surface after washing. In some embodiments, the at least one vegetable may be washed with a soap. In some embodiments, the at least one vegetable may be washed with a surfactant. During the washing step, the at least one vegetable may be agitated and/or scrubbed with the soap, detergent, and/or surfactant in water (or some other applicable solvent). In some embodiments, the at least one vegetable is washed in water, preferably warm water ranging in temperature from about 30 to about 45° C. In some embodiments, the warm water ranges from about 32 to about 40° C. The whole leaf vegetables described herein are never blanched.

After washing, in some embodiments, the at least one washed whole leaf vegetable may be rinsed with a material suitable for removing any excess soap, detergent, and/or surfactants. In some embodiments, the at least one washed whole leaf vegetable is rinsed with water, preferably cold water ranging in temperature from about 10 to about 27° C.

In some embodiments, the powders described herein are free-flowing and do not form clumps due to the particle size and/or moisture content of the powder produced. In some embodiments, the powder can be sprinkled directly onto food to provide the nutrients still found in the powder while limiting the effects of taste and texture that is commonly found when raw vegetable(s) are simply combined to food. For example, the addition of a raw whole kale leaf onto a hamburger will add the flavor and texture of the raw whole kale leaf to the hamburger thereby altering the flavor and texture of the hamburger overall. However, when the free-flowing powders described herein are combined with a hamburger, either during formation of the hamburger and/or added on top of the burger after formation, the significantly reduced particle size of the powder affects the texture and taste of the hamburger significantly less if not at all (as compared to the raw whole leaf) while still providing the many of the nutrients found in the raw whole leaf, i.e., vitamins, minerals, antioxidants, proteins, etc.

In some embodiments, the powders described herein are free-flowing and configured to be delivered into the body of a patient via a pharmaceutically acceptable carrier. For example, the vegetable(s) powders described herein may be further processed into a tablet and/or capsule form for oral delivery. In another example, the vegetable powders described herein may be further processed into a suppository form for rectal delivery. In still other examples, the vegetable powders described herein may be further compounded into a pharmaceutically acceptable base suitable for topical delivery.

In some embodiments, the vegetable powder described herein includes only the vegetable(s) without any additional agents and/or ingredients.

In some embodiments, the vegetable powder described herein includes only a single vegetable without any additional agents and/or ingredients.

In some embodiments, the vegetable powder described herein includes only a single vegetable which is a green leafy vegetable without any additional agents and/or ingredients.

In some embodiments, the vegetable powder described herein includes only a single vegetable which is a green vegetable without any additional agents and/or ingredients.

In some embodiments, the vegetable powder described herein includes only a single vegetable which is kale without any additional agents and/or ingredients.

In some embodiments, a vegetable powder described herein may be combined with at least one additional agent and/or ingredient to form a vegetable composition, in powder or non-powder form.

In some embodiments, a green vegetable powder described herein may be combined with at least one additional agent and/or ingredient to form a green vegetable composition, in powder or non-powder form.

In some embodiments, a green leafy vegetable powder described herein may be combined with at least one additional agent and/or ingredient to form a green leafy vegetable composition, in powder or non-powder form.

In some embodiments, a kale powder as described herein may be combined with at least one additional agent and/or ingredient to form a kale composition, in powder or non-powder form. Examples of additional agents and/or ingredients used to form a vegetable (e.g., green, green leafy, and/or kale, specifically, as well as any of the other vegetable(s) described herein) composition include at least one: pharmaceutically acceptable carrier (e.g., diluents, topical base materials, rectal base materials, oral base materials, sterile materials suitable for injection, etc.), therapeutic agent (e.g., drugs, antibodies, blood products, etc.), optional ingredient (e.g., preservatives, dyes, binders, emulsifiers, ph modifiers, etc.), other food-related product (e.g., seasonings, powdered drinks, coffee, tea, flours, cake mixes, candy, granola bars, chocolates, gums, cereals, breads, pastas, etc.), and/or health and beauty aid (make-up, skin moisturizers, sunblock, sun tanning lotions, lip balms, anti-wrinkle, hair growth, shampoo, conditioner, hair dye, toothpaste, mouthwash, etc.).

Reference made herein to vegetable composition is intended to encompass any vegetable composition, including the specific green, green leafy, and/or kale compositions recited hereinabove, as well as any vegetable composition formed from any of the other suitable vegetable(s) provided hereinabove, i.e., carrot composition, artichoke composition, root vegetable composition, kale and carrot composition, etc.).

In some embodiments, the vegetable composition includes at least one of a pharmaceutically acceptable carrier. As used herein the term "pharmaceutically acceptable carrier" refers to a non-toxic solid, semisolid or liquid filler, diluent, encapsulating material, formulation auxiliary, or excipient of any conventional type. A pharmaceutically acceptable carrier is nontoxic to recipients at the dosages and concentrations employed and is compatible with other ingredients of the vegetable composition. Some well-known pharmaceutically acceptable carriers include, but are not limited to, saline, phosphate buffered saline, water, dextrose, and lactated ringers.

Additionally, such pharmaceutically acceptable carriers may be aqueous or non-aqueous solutions, suspensions, colloids, and emulsions. Examples of non-aqueous solvents are alcohols, propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Topical carriers include creams, ointments, gels, jellies, solutions, and the like. Preservatives and other additives may also be present, such as, for example, antimicrobials, antioxidants, collating agents, inert gases and the like.

In some embodiments, the vegetable composition may be in the form of a solution or suspension. It is envisioned that the vegetable composition, solution or suspension may be applied topically, injected, rectally inserted, intranasally sprayed, and/or orally ingested.

In some embodiments, a topical skin treatment may be created by combining the vegetable composition with the appropriate surfactants to maintain contact between the skin surface and vegetable composition. Commonly used surfactants appropriate for personal care products include, but are not limited to sodium lauryl sulfate, ammonium laureth sulfate, disodium lauryl sulfosuccinate, cocamphocarboxyglycinate, cocoamidopropyl betaine, and alpha-olefin sulfonate. Alternatively, surfactants made from plant-derived oils may be used instead of surfactants made from petroleum or synthetic oils. These plant derived oils may also be combined with ethoxylates to increase performance. Coloring agents and fragrances may be added to produce a more marketable product.

In some embodiments, a spot treatment including the vegetable powder and/or composition may also be created. By combining the vegetable powder with the appropriate surfactants discussed above a vegetable composition could be created for spot treating small areas a customer fears may contain or developing cancerous cells, i.e., basal carcinoma, melanoma cells, etc. This product may have fewer coloring and fragrance concerns but may still need to include the necessary surfactants to allow for long term contact between the vegetable composition and any potentially cancerous or precancerous cells.

In some embodiments, a spa treatment involving the combination of the vegetable powder and appropriate surfactants, which may include muds or clays to treat large portions of a person's body topically. A person may submerge himself in a large container, possibly a bathtub, containing a combination of the vegetable powder and the appropriate surfactants, adjuvants, colorants, or fragrances.

The surfactant may represent from 0%/o by weight to about 25% by weight of the vegetable composition. In some embodiments, the surfactant may represent from about 0.01% by weight to about 20% by weight of the vegetable composition. In still other embodiments, the surfactant may represent from about 1% by weight to about 10% by weight of the vegetable composition.

In some embodiments, the vegetable compositions may include at least one optional ingredient. Some examples of useful optional ingredients include, but are not meant to be limited to, pH-modifiers, emulsifiers, lyposomes, microspheres, beads, viscosity enhancers, humectants, colors, fragrances, and the like. The optional ingredients typically represent less than about 10% by weight of the vegetable composition, in some embodiments, less than about 5% by weight of the vegetable composition.

It is further envisioned that the vegetable compositions described herein may also be administered by intravenous, intraarterial, intramuscular or intratumoral injection of a liquid preparation, oral administration of a liquid or solid preparation including oral solutions, tablets, or capsules for oral ingestion, or by spray solution suitable for nasal spray, oral spray, topical spray, or rectal spray. Administration can also be accomplished by use of a rectal suppository or a urethral suppository.

A range of carrier mediums would be suitable for the topical administration of the vegetable compositions described herein. This would include ointments, creams, gels, jellies or other application. The properties of a suitable topical formulation would be one that is easy to apply to a reasonable large area of tissue, requiring the minimum of rubbing and lasting in contact with the tissue from at least a few hours to a few days.

It is further envisioned that the vegetable compositions described herein may further include at least one therapeutic agent in addition to the vegetable powder. Some non-limiting examples of suitable therapeutic agents include: analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate); antiasthmatics (e.g., ketotifen and traxanox); antibiotics (e.g., neomycin, streptomycin, chloramphenicol, cephalosporin, ampicillin, penicillin, tetracycline, and ciprofloxacin); antidepressants (e.g., nefopam, oxypertine, doxepin, amoxapine, trazodone, amitriptyline, maprotiline, phenelzine, desipramine, nortriptyline, tranylcypromine, fluoxetine, imipramine, imipramine pamoate, isocarboxazid, trimipramine, and protriptyline); antidiabetics (e.g., biguanides and sulfonylurea derivatives); antifungal agents (e.g., griseofulvin, ketoconazole, itraconazole, amphotericin B, nystatin, and candicidin); antihypertensive agents (e.g., propanolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine); anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, deflazacort, celecoxib, rofecoxib, hydrocortisone, prednisolone, and prednisone); antineoplastics (e.g., cyclophosphamide, actinomycin, bleomycin, dactinomycin, daunorubicin, doxorubicin, epirubicin, mitomycin, methotrexate, fluorouracil, gemcitabine, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, goserelin, leuprolide, tamoxifen, interferon alfa, retinoic acid (ATRA), nitrogen mustard alkylating agents, and piposulfan); antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene); immunosuppressive agents (e.g., cyclosporine, azathioprine, mizoribine, and FK506 (tacrolimus)); antimigraine agents (e.g., ergotamine, propanolol, isometheptene mucate, and dichloralphenazone); sedatives/hypnotics (e.g., barbiturates such as pentobarbital, pentobarbital, and secobarbital; and benzodiazapines such as flurazepam hydrochloride, triazolam, and midazolam); antianginal agents (e.g., beta-adrenergic blockers; calcium channel blockers such as nifedipine, and diltiazem; and nitrates such as nitroglycerin, isosorbide dinitrate, pentearythritol tetranitrate, and erythrityl tetranitrate); antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine); antimanic agents (e.g., lithium carbonate); antiarrhythmics (e.g., bretylium tosylate, esmolol, verapamil, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine); antiarthritic agents (e.g., phenylbutazone, sulindac, penicillanine, salsalate, piroxicam, azathioprine, indomethacin, meclofenamate, gold sodium thiomalate, ketoprofen, auranofin, aurothioglucose, and tolmetin sodium); antigout agents (e.g., colchicine, and allopurinol); anticoagulants (e.g., heparin, heparin sodium, and warfarin sodium); thrombolytic agents (e.g., urokinase, streptokinase, and alteplase); antifibrinolytic agents (e.g., aminocaproic acid); hemorheologic agents (e.g., pentoxifylline); antiplatelet agents (e.g., aspirin); anticonvulsants (e.g., valproic acid, divalproex sodium, phenytoin, phenytoin sodium, clonazepam, primidone, phenobarbital, carbamazepine, amobarbital sodium, methsuximide, metharbital, mephobarbital, mephenytoin, phensuximide, paramethadione, ethotoin, phenacemide, secobarbital sodium, clorazepate dipotassium, and trimethadione); antiparkinson agents (e.g., ethosuximide); antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, methdilazine, and); agents useful for calcium regulation (e.g., calcitonin, and parathyroid hormone); antibacterial agents (e.g., amikacin sulfate, aztreonam, chloramphenicol, chloramphenicol palmitate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate); antiviral agents (e.g., interferon alpha, beta or gamma, zidovudine, amantadine hydrochloride, ribavirin, and acyclovir); antimicrobials (e.g., cephalosporins such as cefazolin sodium, cephradine, cefaclor, cephapirin sodium, ceftizoxime sodium, cefoperazone sodium, cefotetan disodium, cefuroxime axetil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; macrolides such as, azithromycin, clarithromycin, and erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride); anti-infectives (e.g., GM-CSF); bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and theophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; salmeterol; xinafoate; triamcinolone; nedocromil sodium; flunisolide; fluticasone propionate; steroidal compounds and hormones (e.g., androgens such as danazol, testosterone cypionate, fluoxymesterone, ethyltestosterone, testosterone enathate, methyltestosterone; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and thyroid hormones such as levothyroxine sodium); hypoglycemic agents (e.g., human insulin, purified beef insulin, purified pork insulin, glyburide, metformin, chlorpropamide, glipizide, tolbutamide, and tolazamide); hypolipidemic agents (e.g., clofibrate, dextrothyroxine sodium, probucol, pravastitin, atorvastatin, lovastatin, and niacin); proteins (e.g., DNase, alginase, superoxide dismutase, and lipase); nucleic acids (e.g., sense or anti-sense nucleic acids encoding any therapeutically useful protein, including any of the proteins described herein); agents useful for erythropoiesis stimulation (e.g., erythropoietin); antiulcer/antireflux agents (e.g., famotidine, cimetidine, and ranitidine hydrochloride); antinauseants/antiemetics (e.g., meclizine hydrochloride, nabilone, prochlorperazine, dimenhydrinate, promethazine hydrochloride, thiethylperazine, and scopolamine); as well as other drugs useful in the compositions and methods described herein include mitotane, halonitrosoureas, anthrocyclines, ellipticine, ceftriaxone, ketoconazole, ceftazidime, oxaprozin, valacyclovir, urofollitropin, famciclovir, flutamide, enalapril, itraconazole, buspirone, gabapentin, fosinopril, tramadol, acarbose, lorazepam, follitropin, omeprazole, fluoxetine, lisinopril, tramadol, levofloxacin, zafirlukast, interferon, growth hormone, interleukin, erythropoietin, granulocyte stimulating factor, nizatidine, bupropion, perindopril, erbumine, adenosine, alendronate, alprostadil, benazepril, betaxolol, bleomycin sulfate, dexfenfluramine, diltiazem, fentanyl, flecainide, gemcitabine, glatiramer acetate, granisetron, lamivudine, mangafodipir trisodium, mesalamine, metoprolol fumarate, metronidazole, miglitol, moexipril, monteleukast, octreotide acetate, olopatadine, paricalcitol, somatropin, sumatriptan succinate, tacrine, verapamil, nabumetone, trovafloxacin, dolasetron, zidovudine, finasteride, tobramycin, isradipine, tolcapone, enoxaparin, fluconazole, lansoprazole, terbinafine, pamidronate, didanosine, diclofenac, cisapride, venlafaxine, troglitazone, fluvastatin, losartan, imiglucerase, donepezil, olanzapine, valsartan, fexofenadine, calcitonin, and ipratropium bromide; and combinations thereof.

The therapeutic agents may be used in amounts that are therapeutically effective, which varies widely depending largely on the particular therapeutic agent being used. The amount of therapeutic agent incorporated into the vegetable composition also depends upon the desired release profile, the concentration of the agent required for a biological effect, and the length of time that the therapeutic agent should be released for treatment.

The vegetable powder and any of the pharmaceutically acceptable carrier, the surfactant, the optional ingredient and/or the therapeutic agent may be combined in any manner known to those of ordinary skill in the art. Some non-limiting examples include simply mixing the ingredients after vegetable powder formation and prior to distribution. In other examples the ingredients may be maintained separately until use and only combined immediately prior to use for stability purposes. Alternatively, it is envisioned that the vegetable powders described herein may in some embodiments be administered alone and/or sequentially with any of the other agents and/or ingredients described herein.

The vegetable compositions described herein may be formulated to be compatible with the intended route of administration. For example, topical applications may be formed into sterile or non-sterile solutions depending upon the tissue intended to be applied. For example, topical application to the external tissue of a patient's skin does not necessarily have to be sterilized. However, topical application of an inhalation powder or spray and/or application in the form of an eye drop may require sterilization. In some embodiments, wherein the chemopreventative composition is sterilized, the composition may be exposed to UV radiation, a gas sterilization process, a heat sterilizing process, and/or a microfiltering process.

In additional examples, the vegetable powders and/or compositions may be formed into orally-ingesting forms, including oral solutions, tablets, capsules, dissolvable films, etc., and thus may not require sterilization.

In still other embodiments, the vegetable powders and/or compositions may be intended to be injected, i.e., intramuscularly, intravenously, subcutaneously, intratumorally, intralesionally, the vegetable composition may be formed into sterile solutions, suspensions, dispersions, or emulsions including carriers or diluents such as water for injection, saline solution, polyethylene glycols, glycerine, propylene glycol or other synthetic solvents; anti-bacterial agents such as benzyl alcohol or methylparabens; antioxidants such as ascorbic acid or sodium bisulfite; buffers such as acetates, citrates or phosphates, and agents for the adjustment of tonicity such as sodium chloride or dextrose. The pH may be adjusted with acids or bases, such as hydrochloric acid or sodium hydroxide, as needed. Preparations may be enclosed in ampules, disposable syringes or multiple dose vials made of glass or plastic.

The vegetable powders and/or compositions described herein may be stored in a kit, container, pack or dispenser. In some embodiments, the kit may include multiple containers wherein the vegetable powder and any additional ingredients may be stored separately and combined immediately prior to use to prolong shelf-life of the ingredients of the vegetable composition. In some embodiments, the ingredients of the vegetable compositions may be combined prior to storage and contained in a single container. In yet other embodiments, the ingredients of the vegetable compositions may be combined prior to storage and stored in multiple containers representing individual doses of the vegetable composition.

In some embodiments, the kits include a vegetable powder or composition, as described herein, in a single container, the container configured to dispense the vegetable powder over food. In embodiments, the container is a shaker. In some embodiments, the container includes a flip top suitable for dispensing the vegetable powder or composition via shaking or sprinkling. In some embodiments, a portion of the top is perforated.

In some embodiments, the container is opaque thereby preventing light to pass thru to prevent the breakdown of the vegetable powder or composition contained therein.

In addition, the kits described herein may also include additional tools or objects including, but not limited to, a syringe, a needle, a straw, delivery tools such as a pad or sponge for topical delivery, measuring cups or mixing cups for orally-ingested solutions. The vegetable powders and/or compositions included in any of the kits may be supplied in containers of any sort such that the life of the different components may be preserved and may not be adsorbed or altered by the materials of the container. For example, sealed glass ampules or vials may contain the compositions described herein that have been packaged under a neutral non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include bottles that are fabricated from similar substances as ampules, and envelopes that consist of foil-lined interiors, such as aluminum or an alloy. Other containers include test tubes, vials, flasks, bottles, syringes, sealable plastic baggies, shakers, etc. Some containers may have a sterile resealable access port, such as a bottle having a stopper that may be pierced repeatedly by a hypodermic injection needle.

The present disclosure further provides methods of use of vegetable powders and/or compositions described herein, such as for 1) treating a mammalian subject with cancer; 2) suppressing or inhibiting cancer in a mammalian subject; 3) reducing the risk of developing cancer in a mammalian subject; 4) treating precancerous lesions in a mammalian subject; 5) suppressing or inhibiting precancerous lesions in a mammalian subject; 6) reducing the amount of precancerous lesions in a mammalian subject; by administering the vegetable powders or compositions directly to the lesion; 7) reducing the amount of cancer and/or precancerous lesions in a mammalian subject, by topically applying the vegetable powders or compositions to the cancer and/or precancerous lesion; 8) being non-toxic to non-cancerous cells; and, 9) increasing the amount of non-cancerous cells. In one embodiment the subject is a mammalian subject. In another embodiment the subject is a human subject.

The present disclosure also provides methods of use of vegetable powders or compositions described herein, such as for 1) treating a mammalian subject with melanoma; 2)

suppressing or inhibiting melanoma in a mammalian subject; 3) reducing the risk of developing melanoma in a mammalian subject; 4) treating premelanoma lesions in a mammalian subject; 5) suppressing or inhibiting premelanoma lesions in a mammalian subject; 6) reducing the amount of premelanoma lesions in a mammalian subject; by administering the vegetable powders or compositions as provided hereinabove; 7) reducing the amount of melanoma and/or premelanoma lesions in a mammalian subject, by topically applying the vegetable powders or compositions to the melanoma and/or premelanoma lesion; 8) reducing the amount of melanoma and/or premelanoma lesions in a mammalian subject, by orally-ingesting the vegetable powders or compositions on a daily basis for at least week, month, and/or year; 9) being non-toxic to non-cancerous epithelial; and, 10) increasing the amount of non-cancerous epithelial cells. In one embodiment the subject is a mammalian subject. In another embodiment the subject is a human subject.

The present disclosure also provides methods of use of vegetable powders or compositions described herein, such as for 1) treating a mammalian subject with basal cell carcinoma or skin tags; 2) suppressing or inhibiting basal cell carcinoma or skin tags production in a mammalian subject; 3) reducing the risk of developing basal cell carcinoma or skin tags in a mammalian subject; 4) treating prebasal cell carcinoma or pre-skin tags lesions in a mammalian subject; 5) suppressing or inhibiting prebasal cell carcinoma or pre-skin tags lesions in a mammalian subject; 6) reducing the amount of prebasal cell carcinoma or pre-skin tags lesions in a mammalian subject; by administering the vegetable powders or compositions to the prebasal cell carcinoma; 7) reducing the amount of basal cell carcinomas, prebasal cell carcinoma, skin tags, or pre-skin tag lesions in a mammalian subject, by topically applying the vegetable powders or compositions to the basal cell carcinomas, prebasal cell carcinoma, skin tags, or pre-skin tag lesion; 8) reducing the amount of basal cell carcinomas, prebasal cell carcinoma, skin tags, or pre-skin tag lesions in a mammalian subject, by orally-ingesting the vegetable powders or compositions on a daily basis for at least week, month, and/or year; 9) being non-toxic to non-cancerous epithelial cells; and, 10) increasing the amount of non-cancerous epithelial cells. In one embodiment the subject is a mammalian subject. In another embodiment the subject is a human subject.

In one embodiment, a method of inducing apoptosis in cancer cells includes applying vegetable powders or compositions including kale to cancer cells. The kale of the vegetable powders or compositions may be selected from the group consisting of curly kale, baby kale, organic kale, kale harvested during seeding time, and combinations thereof.

In some embodiments, the kale of the vegetable powders or compositions includes curly kale.

In some embodiments, the vegetable powders or compositions can be applied to or used to treat cancer cells selected from the group consisting of melanoma cells, breast cancer cells, colon cancer cells, ovarian cancer cells, prostate cancer cells, brain cancer cells, bone cancer cells, bladder cancer cells, testicular cancer cells, thyroid cancer cells, lung cancer cells, liver cancer cells, pancreatic cancer cells, throat cancer cells, and combination thereof.

In some embodiments, the cancer cells include melanoma cells.

In some embodiments, the step of applying the vegetable powders or compositions includes topical delivery.

In some embodiments, the method of inducing apoptosis in cancer cells further includes applying the vegetable powder or composition to non-cancerous cells, wherein the vegetable powders or composition is non-toxic to the non-cancerous cells and/or the vegetable powder or composition promotes the growth of the non-cancerous cells.

In some embodiments, the non-cancerous cells are epithelial cells.

In some embodiments, the method of inducing apoptosis in cancer cells further includes maintaining interaction between the vegetable powder and/or composition and the cancer cells for more than 7 hours.

In some embodiments, the method of inducing apoptosis in cancer cells further includes maintaining interaction between the vegetable powder and/or composition and the cancer cells for more than 20 hours.

In some embodiments, the vegetable powder and/or composition is deliverable to the cancer cells in a form selected from the group consisting of intravenously, intramuscularly, subcutaneously, intratumorally, topically, orally, transdermally, sublingually, via nasal inhalation, via oral inhalation, via suppository, and combinations thereof.

In some embodiments, the vegetable powder and/or composition induces apoptosis in cancer cells selected from the group consisting of melanoma cells, breast cancer cells, colon cancer cells, ovarian cancer cells, prostate cancer cells, brain cancer cells, bone cancer cells, bladder cancer cells, testicular cancer cells, thyroid cancer cells, lung cancer cells, liver cancer cells, pancreatic cancer cells, throat cancer cells, and combination thereof.

In some embodiments, the vegetable powder and/or composition induces apoptosis in cancer cells including melanoma cells.

In some embodiments, the vegetable powder and/or composition is non-toxic to non-cancerous cells.

In some embodiments, the vegetable powder and/or composition promotes growth of the non-cancerous cells.

In some embodiments, the non-cancerous cells are epithelial cells.

In some embodiments, the cancerous or precancerous skin lesions include basal cell carcinoma. In some embodiments, the cancerous or precancerous skin lesions include skin tags.

In some embodiments, the vegetable powder and/or composition is non-toxic to non-cancerous and non-precancerous cells.

In some embodiments, the vegetable powder and/or composition promotes the growth of the non-cancerous and non-precancerous cells.

In some embodiments, the non-cancerous cells are epithelial cells.

In some embodiments, the method of reducing cancerous or precancerous skin lesions, further includes repeating the step of orally-ingesting the vegetable powder and/or composition on at least a daily basis for at least one week.

In some embodiments, the method of reducing cancerous or precancerous skin lesions, further includes repeating the step of orally-ingesting the vegetable powder and/or composition on at least a daily basis for at least one month.

In some embodiments, the method of reducing cancerous or precancerous skin lesions, further includes repeating the step of orally-ingesting the vegetable powder and/or composition on at least a daily basis for at least three months.

In some embodiments, the method of reducing cancerous or precancerous skin lesions, further includes repeating the step of orally-ingesting the c vegetable powder and/or composition on at least a daily basis for at least six months.

In some embodiments, the method of reducing cancerous or precancerous skin lesions, further includes repeating the step of orally-ingesting the vegetable powder and/or composition on at least a daily basis for at least one year.

In some embodiments, the step of orally-ingesting the vegetable powder and/or composition is performed once a day.

In some embodiments, the step of orally-ingesting the vegetable powder and/or composition is performed more than once a day.

In some embodiments, the step of orally-ingesting the vegetable powder and/or composition is performed twice a day.

In some embodiments, the step of orally-ingesting the vegetable powder and/or composition is performed four times a day.

In some embodiments, the vegetable powders and/or compositions may be added to a gelatin capsule for oral delivery. In some embodiments, at least one of the vegetables is kale. In some embodiments, the only vegetable is kale. The gelatin capsules can be of any size, such as 00, 0, 1, 2, etc. The gelatin capsules can include, e.g., the vegetable powder or composition in the range of about 0.05 to 1500 mg, 0.05 to 1250 mg, 0.05 to 1000 mg, 0.05 to 750 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.1 to 1500 mg, 0.1 to 1250 mg, 0.1 to 1000 mg, 0.1 to 750 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 1500 mg, 0.5 to 1250 mg, 0.5 to 1000 mg, 0.5 to 750 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 1500 mg, 1 to 1000 mg, 1 to 500 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 1500 mg, 5 to 1000 mg, 5 to 500 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 1500 mg, 10 to 1000 mg, 10 to 500 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 1500 mg, 15 to 1000 mg, 15 to 500 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 1500 mg, 20 to 1000 mg, 20 to 500 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 1500 mg, 25 to 1000 mg, 25 to 500 mg, 25 to 300 mg, 25 to 250 mg, 25 to 200 mg, 25 to 175 mg, 25 to 150 mg, 25 to 125 mg, 25 to 100 mg, 25 to 75 mg, 25 to 50 mg, 25 to 30 mg, 30 to 1500 mg, 30 to 1000 mg, 30 to 500 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 35 to 1500 mg, 35 to 1000 mg, 35 to 500 mg, 35 to 300 mg, 35 to 250 mg, 35 to 200 mg, 35 to 175 mg, 35 to 150 mg, 35 to 125 mg, 35 to 100 mg, 35 to 75 mg, 35 to 50 mg, 40 to 1500 mg, 40 to 1000 mg, 40 to 500 mg, 40 to 300 mg 40 to 250 mg, 40 to 200 mg, 40 to 175 mg, 40 to 150 mg, 40 to 125 mg, 40 to 100 mg, 40 to 75 mg, 40 to 50 mg, 50 to 1500 mg, 50 to 1000 mg, 50 to 500 mg, 50 to 300 mg, 50 to 250 mg, 50 to 200 mg, 50 to 175 mg, 50 to 150 mg, 50 to 125 mg, 50 to 100 mg, 50 to 75 mg, 75 to 1500 mg, 75 to 1000 mg, 75 to 500 mg, 75 to 300 mg, 75 to 250 mg, 75 to 200 mg, 75 to 175 mg, 75 to 150 mg, 75 to 125 mg, 75 to 100 mg, 100 to 1500 mg, 100 to 1000 mg, 100 to 500 mg, 100 to 300 mg, 100 to 250 mg, 100 to 200 mg, 100 to 175 mg, 100 to 150 mg, 100 to 125 mg, 125 to 1500 mg, 125 to 1000 mg, 125 to 500 mg, 125 to 300 mg, 125 to 250 mg, 125 to 200 mg, 125 to 175 mg, 125 to 150 mg, 150 to 1500 mg, 150 to 1000 mg, 150 to 500 mg, 150 to 300 mg, 150 to 250 mg, 150 to 200 mg, 150 to 175 mg, 175 to 1500 mg, 175 to 1000 mg, 175 to 500 mg, 175 to 300 mg, 175 to 250 mg, 175 to 200 mg, 200 to 1500 mg, 200 to 1000 mg, 200 to 500 mg, 200 to 300 mg, 200 to 250 mg, 250 to 1500 mg, 250 to 1000 mg, 250 to 500 mg, 250 to 300 mg, 7.5 to 15 mg, 2.5 to 5 mg, 1 to 5 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg.

Suitable dosages may be administered to a subject having once, twice, three or four times daily, every other day, once weekly, or once a month.

It will be understood that various modifications may be made to the embodiments disclosed herein. For example, the compositions may include more than one type of juiced kale. Thus, those skilled in the art will envision other modifications within the scope and spirit of the claims.

Example 1

Approximately 1 teaspoon of liquid detergent, i.e., Dawn® (a registered trademark of Proctor and Gamble) dishwashing soap, was added to 4 gallons of warm water for washing of naturally raw whole leaf vegetable, such as kale. The warm water ranging in temperature from about 30 to about 45° C., and specifically about 32° C. The raw whole leaf vegetable was briskly agitated and washed with the soapy water for up to 15 minutes, and specifically for about 5-15 minutes.

The soapy water was then drained from the raw whole leaf vegetable and the raw whole leaf vegetable was rinsed in over 4 gallons of fresh cold water for up to 15 minutes, and specifically about a ten-minute period. The cold water ranging in temperature from about 5 to about 27° C., and specifically about 10° C. This rinsing procedure was repeated up to 7 consecutive times until most, if not all, of the detergent was removed. In the case of kale, the washed and rinsed raw whole leaf vegetable displayed a shine not formerly displayed on the raw whole leaf vegetable as originally provided.

The washed and rinsed raw whole leaf vegetable was then chilled for a period of time ranging from about 60 minutes to about a week, and specifically about 3 days, by exposing the washed and rinsed raw whole leaf vegetable to a temperature less than 0° C., and specifically about −20° C. to form a chilled (frozen) raw whole leaf vegetable.

The chilled raw whole leaf vegetable was then heated to form a dry whole leaf vegetable, i.e., dry whole leaf kale. The whole leaf vegetable was exposed to a temperature ranging from about 96 to about 106 degrees Fahrenheit and specifically about 105 degrees Fahrenheit, for about 3 to 18 hours to form a dried and/or dehydrated whole leaf vegetable, i.e., dry whole leaf kale. After heating, the whole leaf vegetable contained a moisture content that was less than about 100%, and specifically between about 5% and about 7.5%.

The dry whole leaf vegetable, i.e., dry whole leaf kale, was then comminuted by grinding the whole leaf vegetable into a fine free-flowing vegetable powder. The average particle size of the powder ranged from 0.1 to about 900 microns, and specifically about less than about 500 microns.

The nutritional value of the fine, free-flowing vegetable powder, i.e., fine, free-flowing kale powder, produced is provided below in Table 1 along with the nutritional value of the raw whole leaf kale as originally provided prior to washing.

least one ingredient selected from the group consisting of folate, calcium, vitamin E, vitamin K, niacin, magnesium, phosphorous, zinc, tryptophan, quercetin, kaemperfol, and combinations thereof, as compared to the nutritional value of the whole leaf vegetable or kale prior to processing. The amount of tryptophan, when compared not only to the whole leaf kale, but other excellent sources of tryptophan, such as meat, chicken, or turkey, is very high per 100 g sample.

According to common scientific analysis, the percent difference between the nutritional quantity between the kale powder of Example 1 and the original unprocessed whole leaf kale is within normal variances and the nutritional value is at least about 90%.

In some embodiments, the produce vegetable powders which generally retains at least 50% of the nutritional value of the whole leaf vegetable prior to processing. As shown, in

TABLE 1

| 100 g of whole leaf kale | Amount | Unit | DV % | 8 g of kale powder Amount | Unit | DV % | % diff. |
|---|---|---|---|---|---|---|---|
| Nutrition Facts | | | | | | | |
| Calories | 35 | cal | 1.75 | 23.6 | cal | 1.77 | 67.43 |
| Protein | 2.92 | g | 5.84 | 2.096 | g | 6.288 | 70.54 |
| Total Fat | 1.49 | g | 2.292307692 | 0.456 | g | 1.05230769 | 70.47 |
| Ash | 1.54 | g | 0 | 0.864 | g | 0 | 56.10 |
| Carbohydrate | 4.42 | g | 1.473333333 | 4.216 | g | 2.108 | 95.38 |
| Fiber | 4.1 | g | 16.4 | 1.984 | g | 11.904 | 48.39 |
| Sugars | 0.99 | g | 1.98 | 0.808 | g | 2.424 | 81.62 |
| Vitamin/Mineral | | | | | | | |
| Vitamin A | 241 | mcg | 26.77777778 | 99.2 | mcg | 16.5333333 | 41.16 |
| Folate | 62 | mcg | 15.5 | 45.76 | mcg | 17.16 | 73.8 |
| Vitamin C | 93.4 | mg | 103.7777778 | 10.88 | mg | 18.1333333 | 11.65 |
| Vitamin D | 0 | mcg | 0 | 0 | mcg | 0 | |
| Calcium | 254 | mg | 19.53846154 | 162.4 | mg | 18.7384615 | 63.94 |
| Iron | 1.6 | mg | 8.888888889 | 0.6512 | mg | 5.42666667 | 40.7 |
| Vitamin E | 1.54 | mg | 10.26666667 | 1.12 | mg | 11.2 | 72.73 |
| Vitamin K | 389.6 | mcg | 324.6666667 | 221.3 | mcg | 277 | 56.8 |
| Thiamin | 0.11 | mg | 9.166666667 | | mg | 0 | |
| Riboflavin | 0.347 | mg | 26.69230769 | | mg | 0 | |
| Niacin | 1.18 | mg | 7.375 | 1.424 | mg | 13.35 | 120.68 |
| Vitamin B6 | 0.147 | mg | 8.647058824 | 0 | mg | 0 | |
| Vitamin B12 | 0 | mcg | 0 | | mcg | 0 | |
| Pantothenic Acid | 0.37 | mg | 7.4 | 0 | mg | 0 | 0 |
| Biotin | 0 | mcg | 0 | | mcg | 0 | |
| Choline | 0.5 | mg | 0.090909091 | 0.04 | mg | 0.01090909 | 8 |
| Chromium | 0 | mcg | 0 | | mcg | 0 | |
| Copper | 0.053 | mg | 5.888888889 | 0.03104 | mg | 5.17333333 | 58.57 |
| Iodine | 0 | mcg | 0 | | mcg | 0 | |
| Magnesium | 33 | mg | 7.857142857 | 24.96 | mg | 8.91428571 | 75.63 |
| Manganese | 0.92 | mg | 40 | 0.216 | mg | 14.0869565 | 23.48 |
| Molybdenum | 0 | mcg | 0 | | mcg | 0 | |
| Phosphorus | 55 | mg | 4.4 | 31.68 | mg | 3.8016 | 57.6 |
| Potassium | 348 | mg | 7.404255319 | 172.8 | mg | 5.51489362 | 49.66 |
| Selenium | 0.9 | mcg | 1.636363636 | 0.072 | mcg | 0.19636364 | 8 |
| Zinc | 0.39 | mg | 3.545454545 | 0.2056 | mg | 2.80363636 | 52.72 |
| Tryptophan | 40 | mg | | 37.44 | mg | | 93.6 |
| Quercetin | 22.6 | mg | | 13.78 | mg | | 60.97 |
| Kaemperfol | 46.8 | mg | | 57.12 | mg | | 122.05 |
| Isohamnetin | 23.6 | mg | | 4.192 | mg | | 17.75 |

As can be seen in Table 1, the processes described herein produce vegetable powders which generally retains at least 50% of the nutritional value of the whole leaf vegetable prior to processing. As shown, in some embodiments, the vegetable powder may be a kale powder which generally retains at least 50% of the nutritional value of the whole leaf kale prior to processing. More specifically, in some embodiments, the vegetable powders and/or kale powders described herein may retain at least 50% of the nutritional value of at some embodiments, the vegetable powder may be a kale powder which generally retains at least 50% of the nutritional value of the whole leaf kale prior to processing.

In addition, in some embodiments, by maintaining the raw whole leaf vegetable throughout the washing and processing steps and not exposing the whole leaf to high temperatures commonly associated with baking of the vegetables to quickly and cheaply reduce moisture content, the vegetable or kale powders described herein are able to retain at least 60% of the nutritional value of flavonols quercetin and kaemperfol, alone or in combination, as compared to the nutritional value of the whole leaf vegetable or kale prior to processing. The intake of flavonols may be associated with decreased risk of depression, cognitive impairment, cardiovascular disease, certain types of cancer, and particularly colon cancer and melanoma, as well as some chronic degenerative diseases in humans. However, flavonols may be easily broken down when exposed to high temperatures over 160° C. when processed or cooked. Thus, in some embodiments, the processes described herein produce vegetable powders or kale powders which retain at least 90% of the kaempferol, as compared to the kaempferol found in the whole leaf vegetable or kale.

In some embodiments, the vegetable powders and/or kale powders described herein may retain at least 60% of the nutritional value of tryptophan, as compared to the nutritional value of the whole leaf vegetable or kale prior to processing. Tryptophan being a precursor for serotonin production.

In some embodiments, the vegetable powders and/or kale powders described herein may retain at least 90% of the nutritional value of tryptophan, as compared to the nutritional value of the whole leaf vegetable or kale prior to processing.

Example 2

The vegetable powder produced in Example 1 was analyzed to determine the amount of pesticides remaining in the vegetable powder and compared to the amount of pesticides remaining in two comparative vegetable (kale) powders formed from known standard methods. The first comparative vegetable powder being washed using a first standard method of washing known as a vinegar washing method and the second comparative vegetable powder being washed using a second standard method of washing vegetables known as a water only method. The whole kale leaf used was collected and grown inorganically from the same farm and processed at the same site using the different processes to compare the resulting powders. The specific pesticides used and their respective amounts after formation of the vegetable powder are provided in detail below in Table 2.

TABLE 2

Sample A (powders formed by the processes described herein) vs. Sample B (powders using water only wash techniques)

| Pesticide name | Sample A (PPM) | Sample B (PPM) | Percentage Decrease | EPA Tolerances (PPM) | Percentage EPA tolerance Decrease |
|---|---|---|---|---|---|
| Azoxystrobin | 0.081 | 1.2 | 93.25 | 25 | 99.68 |
| Bifenthrin | 0.025 | 0.042 | 40.48 | 3.5 | 99.29 |
| Dacthal (DCPA) | 0.091 | 0.13 | 30 | 5 | 98.18 |

Sample C (powders using vinegar wash techniques) vs. Sample B (powders using water only wash techniques)

| Pesticide name | Sample C (PPM) | Sample B (PPM) | Percentage Decrease | EPA Tolerances (PPM) | Percentage EPA tolerance Decrease |
|---|---|---|---|---|---|
| Azoxystrobin | 1.1 | 1.2 | 8.33 | 25 | 95.60 |
| Bifenthrin | 0.028 | 0.042 | 33.33 | 3.5 | 99.20 |
| Dacthal (DCPA) | 0.098 | 0.13 | 24.62 | 5 | 98.04 |

TABLE 2-continued

Sample A (powders formed by the processes described herein) vs. Sample C (powders using vinegar wash techniques)

| Pesticide name | Sample A (PPM) | Sample C (PPM) | Percentage Decrease | EPA Tolerances (PPM) | Percentage EPA tolerance Decrease |
|---|---|---|---|---|---|
| Azoxystrobin | 0.081 | 1.1 | 92.64 | 25 | 99.68 |
| Bifenthrin | 0.025 | 0.028 | 10.71 | 3.5 | 99.29 |
| Dacthal (DCPA) | 0.091 | 0.098 | 7.14 | 5 | 98.18 |

As can be readily seen from the data, the vegetable powders produced herein not only produce vegetable powders having significantly reduced amounts of pesticides than the two comparative powders, but also compared to the acceptable tolerances for safe consumption as set by the Environmental Protection Agency (EPA).

For example, in some embodiments, the vegetable powders described herein, and particularly the kale powders described herein, display at least a 7% reduction in pesticides, as compared to the powders formed using a standard vinegar wash, and display at least a 30% reduction in pesticides, as compare to the powders formed using a standard water only wash. In other examples, and in some embodiments, the vegetable powders described herein, and particularly the kale powders described herein, display a pesticide amount which is less than about 2% of acceptable EPA tolerances, and in some embodiments, display a pesticide amount which is less than about 1% of acceptable EPA tolerances, and in some embodiments, display a pesticide amount which is less than about 0.75% of acceptable EPA tolerances.

In some embodiments, the amount of the pesticide azoxystrobin included in the vegetable or kale powders described herein may be reduced by more than about 90% as compared to the powders formed using processes which utilize a standard vinegar wash or water only wash.

In some embodiments, the amount of the pesticide azoxystrobin included in the vegetable or kale powders described herein may be less than about 0.75% of acceptable EPA tolerances.

In some embodiments, the amount of the pesticide azoxystrobin included in the vegetable or kale powders described herein may be less than about 0.5% of acceptable EPA tolerances.

In some embodiments, the amount of the pesticide bifenthrin included in the vegetable or kale powders described herein may be reduced by more than about 10% as compared to the powders formed using processes which utilize a standard vinegar wash or more than 40% as compared to the powders formed using processes which utilize a water only wash.

In some embodiments, the amount of the pesticide bifenthrin included in the vegetable or kale powders described herein may be less than about 0.75% of acceptable EPA tolerances.

In some embodiments, the amount of the pesticide bifethrin included in the vegetable or kale powders described herein may be less than about 1.0% of acceptable EPA tolerances.

Each of these differences in pesticide amount is not insignificant when you consider these powders are intended for human consumption. In addition, the processes described herein are configured to be performed efficiently both on a small scale, such as by an end consumer, and on a large scale, such as performed by a farmer or distributor of the vegetable powders.

In some embodiments, each of the amounts of pesticides described herein are intended to be regarding vegetable powders or kale powder which uses inorganic vegetables or kale, or any vegetable or kale which, prior to processing, is exposed to the specific pesticide described. In such embodiments, the described pesticide amounts are not intended to cover powders formed from vegetables or kale which were never treated with the pesticide, such as some organic vegetables or kale.

Example 3

The vegetable powder formed in Example 1 was mixed with water and frozen to in a freezer to form ice cubes containing the kale powder described herein.

Example 4

The vegetable powder of Example 1 was added to a shaker container to form a kit suitable for delivering the vegetable powder onto food directly.

Example 5

The vegetable powder of Example 1 was added to a gelatin capsule for oral delivery. No additional agents were added to the powder.

What is claimed is:

1. A method of manufacturing vegetable powder comprising:
   washing at least one whole leaf vegetable in warm water with a detergent to form at least one washed whole leaf vegetable;
   rinsing the at least one washed whole leaf vegetable in cold water to form at least one rinsed whole leaf vegetable;
   chilling the at least one rinsed whole leaf vegetable to a temperature below a freezing point of the whole leaf vegetable to form at least one chilled whole leaf vegetable;
   heating the at least one chilled whole leaf vegetable to a temperature greater than room temperature to form at least one dry whole leaf vegetable; and
   comminuting the at least one dry whole leaf vegetable to form a vegetable powder.

2. The method of claim 1, wherein chilling the at least one rinsed whole leaf vegetable below a freezing point of the whole leaf vegetable comprises exposing the at least one rinsed whole leaf vegetable to a temperature below 0° C.

3. The method of claim 1, wherein chilling the at least one rinsed whole leaf vegetable below a freezing point of the whole leaf vegetable comprises exposing the at least one rinsed whole leaf vegetable to a temperature of about −20° C.

4. The method of claim 1, wherein heating the at least one chilled whole leaf vegetable to a temperature greater than room temperature comprises exposing the at least one chilled whole leaf vegetable to a temperature ranging between about 80° F. to about 150° F.

5. The method of claim 1, wherein heating the at least one chilled whole leaf vegetable to a temperature greater than room temperature comprises exposing the at least one chilled whole leaf vegetable to a temperature ranging between about 90° F. to about 120° F.

6. The method of claim 1, wherein heating the at least one chilled whole leaf vegetable to a temperature greater than room temperature comprises exposing the at least one chilled whole leaf vegetable to a temperature ranging between about 96° F. to about 106° F.

7. The method of claim 1, wherein the at least one dry whole leaf vegetable includes a moisture content of less than about 10%.

8. The method of claim 1, wherein the at least one dry whole leaf vegetable includes a moisture content of less than about 7.5%.

9. The method of claim 1, wherein comminuting comprises grinding the at least one dry vegetable.

10. The method of claim 1, wherein the vegetable powder has a mean particle size ranging from about 10 to 900 microns.

11. The method of claim 10, wherein the mean particle size ranges from about 50 to about 300 microns.

12. The method of claim 1, wherein the at least one whole leaf vegetable is a green leafy vegetable.

13. The method of claim 1 wherein the at least one whole leaf vegetable is kale.

14. A method of manufacturing kale powder comprising:
   washing at least one whole leaf kale in warm water with a detergent to form at least one washed whole leaf kale;
   rinsing the at least one washed whole leaf kale in cold water to form at least one rinsed whole leaf kale;
   freezing the at least one rinsed whole leaf kale to a temperature below about 0° C. to form at least one chilled whole leaf kale;
   heating the at least one chilled whole leaf kale to a temperature ranging from about 90° C. to about 110° C. to form at least one dry whole leaf kale having a moisture content less than about 7.5%; and
   comminuting the at least one dry whole leaf kale to form a kale powder.

15. The method of claim 14, wherein the kale is not blanched.

16. The method of claim 14, wherein the kale powder includes only kale powder.

17. The method of claim 14, wherein the powder has a mean particle size ranging from about 10 to 900 microns.

* * * * *